(12) United States Patent
You et al.

(10) Patent No.: US 9,238,622 B2
(45) Date of Patent: Jan. 19, 2016

(54) CRYSTAL FORM I OF (S)-4-HYDROXY-2-OXO-1-PYRROLIDINE ACETAMIDE, PREPARING METHOD AND USE THEREOF

(75) Inventors: Chao You, Chongqing (CN); Hua Feng, Chongqing (CN); Qi Pang, Chongqing (CN); Lei Ye, Chongqing (CN); Yuying Chen, Chongqing (CN); Zuyuan Rong, Chongqing (CN); Lei Jin, Chongqing (CN); Nan Xu, Chongqing (CN); Fei Li, Chongqing (CN); Bo Li, Chongqing (CN)

(73) Assignee: CHONGQING RUNZE PHARMACEUTICAL CO., LTD., Chongqing (CN)

( * ) Notice: Subject to any disclaimer, the term of this patent is extended or adjusted under 35 U.S.C. 154(b) by 0 days.

(21) Appl. No.: 13/581,821

(22) PCT Filed: Sep. 8, 2010

(86) PCT No.: PCT/CN2010/076721
§ 371 (c)(1),
(2), (4) Date: Aug. 30, 2012

(87) PCT Pub. No.: WO2011/143872
PCT Pub. Date: Nov. 24, 2011

(65) Prior Publication Data
US 2013/0059900 A1    Mar. 7, 2013

(30) Foreign Application Priority Data
May 21, 2010  (CN) .......................... 2010 1 0179812

(51) Int. Cl.
*C07D 207/273*    (2006.01)

(52) U.S. Cl.
CPC ................................. *C07D 207/273* (2013.01)

(58) Field of Classification Search
CPC .................................................. C07D 207/273
See application file for complete search history.

(56) References Cited

U.S. PATENT DOCUMENTS 4,686,296 A    8/1987    Iriuchijima et al.

FOREIGN PATENT DOCUMENTS

| CN | 1956953 A | 5/2007 | |
|---|---|---|---|
| CN | 101575309 A | 11/2009 | |
| CN | 102050774 A | 5/2011 | |
| CN | 102101836 A | 6/2011 | |
| CN | 102249974 A | 11/2011 | |
| CN | 102249975 A | 11/2011 | |
| CN | 101367757 B | 9/2012 | |
| WO | WO 2005115978 | * 12/2005 | ......... C07D 207/273 |

OTHER PUBLICATIONS

Hurst et al., Analytica Chimica Acta, 337 (1997), 233-52.*
Campbell Roberts et al., J. Pharm. Biomed. Anal., 28 (2002) 1149-59.*
Chen et al., J. Pharm. Sci., (1999), v. 88, p. 1191.*
Tiwari et al., J. Pharm. Biomed. Anal., 43 (2007) 865-72.*
Fabbiani et al. (CrystEngComm, 2005, 7(29), 179-186).*
Brittain (Polymorphism in Pharmaceutical Solids, vol. 95, 1999, Taylor & Francis, Harry G. Brittain (Ed.), 427 pp.).*
Morissette et al. (Advanced Drug Delivery Reviews 56 (2004) 275-300).*
Myerson, Handbook of Industrial Crystallization, 2nd Ed (2002), 313 pages.
Mullin, Crystallization, 4th ed. (2001) 594 pages.
Anderson, Chapter 11: Tools for Purifying the Product: Column Chromatograph, Crystallization and Reslurrying, Practical Process Research & Development, 2000, pp. 223-247.
Dyer, Ion Exchange, Encyclopedia of Separation Science, 2000, pp. 156-173.
International Search Report dated Jul. 26, 2012 for PCT/CN2012/074516.

* cited by examiner

*Primary Examiner* — Robert Havlin
(74) *Attorney, Agent, or Firm* — Knobbe, Martens, Olson & Bear, LLP

(57) ABSTRACT

A crystal form I of (S)-4-hydroxy-2-oxo-1-pyrrolidine acetamide, or named (S)-oxiracetam, is provided, which is characterized by a powder x-ray diffraction pattern that exhibits data of d-values versus the relative intensities as: 7.075(M), 5.355(S), 5.092(S), 4.590(M), 4.325(M), 4.259(S), 4.041(VS), 3.808(M), 3.542(M), 3.445(M), 3.393(M), 2.972(M), 2.914(S). A method for preparing a crystal form I of (S)-oxiracetam is also provided, which includes preparing the crude product and crystallizing A use of the crystal form I of (S)-oxiracetam in the manufacture of a medicament for preventing and treating memory dysfunction is also provided. Accordingly, the crystal form I of (S)-oxiracetam prepared by the method has high purity of more than 99.3% based on the percentages of the mass, with better efficacy than (S)-oxiracetam for preventing or treating memory dysfunction. Concerning the way of charging materials, adding inorganic base only a few times is simpler and more beneficial to industrial manufacturing and application.

13 Claims, 3 Drawing Sheets

CRYSTAL FORM I OF (S)-4-HYDROXY-2-OXO-1-PYRROLIDINE ACETAMIDE, PREPARING METHOD AND USE THEREOF

BACKGROUND OF THE INVENTION

1. Field of Invention

The present invention relates to a crystal form of (S)-4-hydroxy-2-oxo-1-pyrrolidine acetamide, a preparing method and a use thereof.

2. Description of the Related Art (S)-4-hydroxy-2-oxo-1-pyrrolidine acetamide is a levorotatory form of oxiracetam, also called commercially (S)-oxiracetam [hereinafter the (S)-oxiracetam]. The chemical structure of (S)-oxiracetam is shown below:

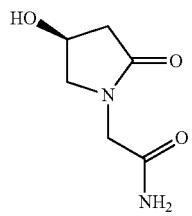

As reported, it is published that oxiracetam is a synthetic cyclic compound derivatives of γ-Amino-β-hydroxybutyric acid (GABOB) is one of the efficacious drugs for Alzheimer's Disease (AD), vascular dementia or the like, which can promote ATP in the brain and the synthesis of acetylcholine, and also enhance transmission of the nerve excitation, improve the retrograde amnesia resulting from lack of oxygen, enhance memory and strengthen learning ability. However, in clinical application, oxiracetam is not ideal for treatment of dementia because of the inefficacious and even antagonistic ingredients therein. It is found in our researches that the efficacy described above of (S)-oxiracetam is much better than that of racemic oxiracetam. Some patents disclose preparation methods of levo-oxiracetam, such like WO/2005115978, CN101367757. CN101367757 discloses a (s)-4-hydroxy-2-oxo-1-pyrrolidine acetamide, which comprises steps of:

(a) adding glycinamide HCl, and partial inorganic bases into alcohol solvent, controlling the pH value being 7.3±0.3, agitating with increasing the temperature and refluxing;

(b) after 2-hour refluxing, adding (S)-4-halo-3-hydroxybutyryl ester, and the surplus inorganic bases in batches at the same time to make the pH value of being ≤8.5 during reaction;

(c) refluxing and reacting after adding (S)-4-halo-3-hydroxybutyryl ester, filtering and concentrating after the reaction finished to obtain a crude product of (S)-4-hydroxy-2-oxo-1-pyrrolidine acetamide;

(d) dissolving the crude product in water and treating the solution with strongly acidic styrene type cation exchange resin as well as collecting products, treating the products with strongly basic styrene type cation exchange resin to neutralize the collected products;

(e) using ethanol to recrystallize the neutralized products, and using isopropanol or methanol/propanol solution to recrystallize the neutralized products again, than obtaining (S)-oxiracetam.

However, it is found that a variety of crystal forms of (S)-oxiracetam exist, depending upon different preparing methods or post-treatment.

SUMMARY OF THE INVENTION

The primary objective of the present invention is to provide a polymorphous (S-4-hydroxy-2-oxo-1-pyrrolidine acetamide in a crystal form which can be applied to the manufacture of a pharmaceutical composition [due to none of related research about crystal forms of (S)-4-hydroxy-2-oxo-1-pyrrolidine acetamide being reported by now, the polymorphous (S-4-hydroxy-2-oxo-1-pyrrolidine acetamide in a crystal form is named as the crystal form I of (S)-4-hydroxy-2-oxo-1-pyrrolidine acetamide, hereinafter called the crystal form I of (S)-oxiracetam]. The crystal form I of (S)-oxiracetam has high purity and the pharmaceutical composition made by thereof has better efficacy for preventing or treating memory dysfunction.

The secondary objective of the present invention is to provide a method for preparing a crystal form I of (S)-oxiracetam. The crystal form I of (S)-oxiracetam prepared by the method has high purity and low impurities therein.

The tertiary objective of the present invention is to provide a use of the crystal form I of (S)-oxiracetam in the manufacture of a medicament for preventing and treating memory dysfunction.

To achieve the objectives, a crystal form I of (S)-oxiracetam in accordance with the present invention is characterized by a powder x-ray diffraction pattern that exhibits data of d-values versus the relative intensities (RI) as shown below:

| d-value | RI | d-value | RI |
| --- | --- | --- | --- |
| 7.075 | M | 5.355 | S |
| 5.092 | S | 4.590 | M |
| 4.325 | M | 4.259 | S |
| 4.041 | VS | 3.808 | M |
| 3.542 | M | 3.445 | M |
| 3.393 | M | 2.972 | M |
| 2.914 | S | | | wherein VS represents "very strong" intensity; S represents "strong" intensity; M represents "moderately strong" intensity.

The crystal form I of (S)-oxiracetam is characterized by a powder x-ray diffraction pattern that exhibits data of d-values versus the relative intensities (RI) as shown below:

| d-value | RI | d-value | RI |
| --- | --- | --- | --- |
| 7.075 | M | 6.348 | W |
| 5.901 | W | 5.355 | S |
| 5.092 | S | 4.590 | M |
| 4.325 | M | 4.259 | S |
| 4.041 | VS | 3.808 | M |
| 3.542 | M | 3.445 | M |
| 3.393 | M | 3.222 | VW |
| 3.171 | W | 2.972 | M |
| 2.914 | S | 2.879 | W |
| 2.813 | W | 2.612 | VW |
| 2.549 | W | 2.424 | W |
| 2.365 | W | 2.138 | VW | wherein VS represents "very strong" intensity; S represents "strong" intensity; M represents "moderately strong" intensity; W represents "weak" intensity; VW represents "very weak" intensity.

The crystal form I of (S)-oxiracetam is characterized by a powder x-ray diffraction pattern with peaks at 12.500, 13.940, 15.000, 16.540, 17.400, 19.320, 20.520, 20.840, 21.980, 23.340, 25.120, 25.840, 26.240, 27.660, 28.100, 30.040, 30.660, 31.040, 31.780, 34.300, 35.180, 37.060, 38.020, and 42.240 degrees in terms of 2θ, according to the powder x-ray diffraction (PXRD) pattern as shown in FIG. 1.

The crystal form I of (S)-oxiracetam is characterized by characteristic absorption bands obtained from infrared spectroscopy at peaks having the wavelengths (cm$^{-1}$) as: hydroxyl group ($v_{O-H}$: 3403 cm$^{-1}$), amido group ($v_{N-H}$: 3355 cm$^{-1}$, 3184 cm$^{-1}$), methylene group ($v_{C-H}$: 2926 cm$^{-1}$, 2881 cm$^{-1}$), carbonyl group ($v_{C=O}$: 1672 cm$^{-1}$, $\delta_{CH2(scissoring)}$: 1489 cm$^{-1}$), hydroxyl group ($\delta_{O-H(in\text{-}plane\ bending)}$: 1399 cm$^{-1}$), primary amido group ($\delta_{N-H}$: 1307 cm$^{-1}$, $\delta_{C-O}$: 1082 cm$^{-1}$), primary amido group ($\delta_{N-H\ (out\text{-}of\text{-}plane\ bending)}$: 672 cm$^{-1}$), according to the infrared (IR) spectrum as shown in FIG. 2.

The crystal form I of (S)-oxiracetam has a differential scanning calorimetric (DSC) peak melting temperature of 139.3° C., according to the differential scanning calorimetric (DSC) thermogram as shown in FIG. 3.

A method for preparing (S)-oxiracetam in accordance with the present invention comprises steps of: preparing a crude product and a post-treatment, wherein the post-treatment comprises the step of: crystallizing the crude product by using acetone and water as solvents.

The water and acetone are in a ratio ranging from 1:5 to 1:20, based on the weight parts.

The step of crystallizing the crude product is performed at low temperature, and more particularly at the temperature of between −10° C. and 10° C.

The step of crystallizing the crude product further comprises steps of: dissolving the crude product in water, adding acetone in drops at the temperature of between −10° C. and 10° C., and agitating for 0.5 hours to 12 hours to obtain a crystalline product; the crude product and the water are in a ratio ranging from 1:0.4 to 1:0.7, the water and the acetone are in a ratio ranging from 1:5 to 1:20, based on the weight parts.

The step of crystallizing the crude product is performed at room temperature, and further comprises the steps of: dissolving the crude product in water, filtering, and agitating with decreasing the temperature to a range of between −10° C. and 10° C., then adding acetone in drops, agitating for 0.5 hours to 12 hours at the same temperature, filtering, and washing with cold acetone to obtain a crystalline product; the crude product and the water are in a ratio ranging from 1:0.4 to 1:0.7, the water and the acetone are in a ratio ranging from 1:5 to 1:20, based on the weight parts.

For further improvement of the purity of the final products obtained from the preparation process, the post-treatment can comprises: refining the crude product before the step of crystallizing the crude product, and specifically, adding ethanol in a weight of 2 to 8 times larger than that of the crude product, then agitating and filtering to obtain a refined product. Alternatively, the post-treatment can also comprises: recrystallizing the crystalline product after the step of crystallizing the crude product.

For distinguishing the two crystalline products made by crystallization and recrystallization, hereinafter the crystalline product made by crystallization is called "the crystalline product", and the other made by recrystallization is called "the recrystalline product".

The step of recrystallizing the crystalline product is using acetone and water as solvents, and the water and acetone are in a ratio ranging from 1:5 to 1:20, based on the weight parts.

The step of recrystallizing the crystalline product is performed at low temperature, and more particularly at the temperature of between −10° C. and 10° C.

The step of recrystallizing the crystalline product further comprises steps of: dissolving the crystalline product in water, adding acetone in drops at the temperature of between −10° C. and 10° C., and agitating for 0.5 hours to 12 hours to obtain a recrystalline product; the crystalline product and the water are in a ratio of from 1:0.4 to 1:0.7, the water and the acetone are in a ratio of from 1:5 to 1:20, based on the weight parts.

The step of recrystallizing the crystalline product is performed at room temperature, and further comprises steps of: dissolving the crystalline product in water, filtering, and agitating with decreasing the temperature to a range of between −10° C. and 10° C., then adding acetone in drops, agitating for 0.5 hours to 12 hours at the same temperature, filtering, and washing with cold acetone to obtain a recrystalline product; the crystalline product and the water are in a ratio ranging from 1:0.4 to 1:0.7, the water and the acetone are in a ratio ranging from 1:5 to 1:20, based on the weight parts.

The post-treatment further comprises the step of: extracting, and the solvent used for extracting is methylene dichloride.

Specifically, the method for preparing (S)-oxiracetam is comprising the steps of:

1. mixing glycinamide HCl, pure ethanol and partial or total sodium bicarbonate and agitating with increasing the temperature and refluxing to carry out the reaction;

2. after refluxing for 2 hours, optionally adding the surplus sodium bicarbonate, and adding (S)-4-chloro-3-hydroxybutyryl acetate in drops, then refluxing and reacting for 24 hours to form a solution, filtering the solution after it being cooled, and then concentrating the filtered solution to make an intermediate product; (S)-4-chloro-3-hydroxybutyryl acetate and glycinamide HCl are in a molar ratio of between 1:0.8 and 1:1.2, (S)-4-chloro-3-hydroxybutyryl acetate and the sodium bicarbonate are in a molar ratio of 1:2, and (S)-4-chloro-3-hydroxybutyryl acetate and the ethanol are in a mole-to-volume ratio of between 1 mole:600 ml and 1 mole:1000 ml;

3. dissolving the intermediate product in water and extracting by using methylene dichloride in a volume of four times larger than that of the water used in dissolving the intermediate product to obtain a solvent extract, concentrating the solvent extract and removing the remaining methylene dichloride, diluting the concentrated solvent extract and passing it through the 001X7 cation exchange resin, collecting product fractions of the concentrated solvent extract, neutralizing the product fractions by cation exchange resin 201X7, then filtering the product fractions to remove the remaining resin therein, concentrating the product fractions and adding charcoal in the middle of the process, then agitating for 30 minutes, filtering and concentrating again to obtain a crude product;

4. crystallizing: adding water to the crude product at room temperature, then filtering, agitating with the decreasing temperature to a range of 2° C. to 5° C., adding acetone in drops, keeping agitating for 30 minutes at the same temperature, then filtering and washing 2 or 3 times with cold acetone to obtain a crystalline product; the crude product and the water are in a ratio ranging from 1:0.4 to 1:0.7, and the water and the acetone are in a ratio ranging from 1:5 to 1:20, based on the weight parts;

5. recrystallizing: dissolving the crystalline product in water at room temperature, filtering, agitating with decreasing the temperature to a range of 2° C. to 5° C., adding acetone in drops to make precipitants, keeping adding acetone and agitating for 30 minutes, then filtering and washing 2 or 3 times with cold acetone to obtain a recrystalline product; the water and the acetone are in a ratio ranging from 1:5 to 1:20, based on the weight parts.

A use of the crystal form I of (S)-oxiracetam in accordance with the present invention is in the manufacture of a medicament for preventing or treating memory dysfunction.

A use of the crystal form I of (S)-oxiracetam in accordance with the present invention is in the manufacture of a medicament for preventing or treating memory dysfunction. Specifically, the crystal form I of (S)-oxiracetam can used as an active ingredient in the manufacture of a pharmaceutical composition, wherein the dosage form thereof can be prepared by common process as an oral dosage form or an injection form. The oral dosage form includes tablets, dripping pills, powder, granules, capsules or the like, while an injection form includes injectable powder, injectable freeze-dried powder or the like.

The dosage form can be preferably capsules, tablets or injection.

The advantages of the present invention are described below:

1. the crystal form I of (S)-oxiracetam can be used in the manufacture of a pharmaceutical composition with better efficacy than other composition manufactured by using (S)-oxiracetam for preventing or treating memory dysfunction.

2. the crystal form I of (S)-oxiracetam prepared by the method of the present invention has high purity of more than 99.3% based on the percentages of the mass.

3. the operation manner of the method of the present invention is simple and easy to handle. With regard to the way of charging materials, adding inorganic base only 1 time or 2 times is much convenient to the industrial manufacturing and application.

4. the method of the invention uses methylene dichloride to extract impurities in the aqueous phase greatly improve the quality of the final products with low impurities of about 0-0.5%, based on the percentages of the mass.

DETAILED DESCRIPTION OF THE INVENTION

Figure 1:
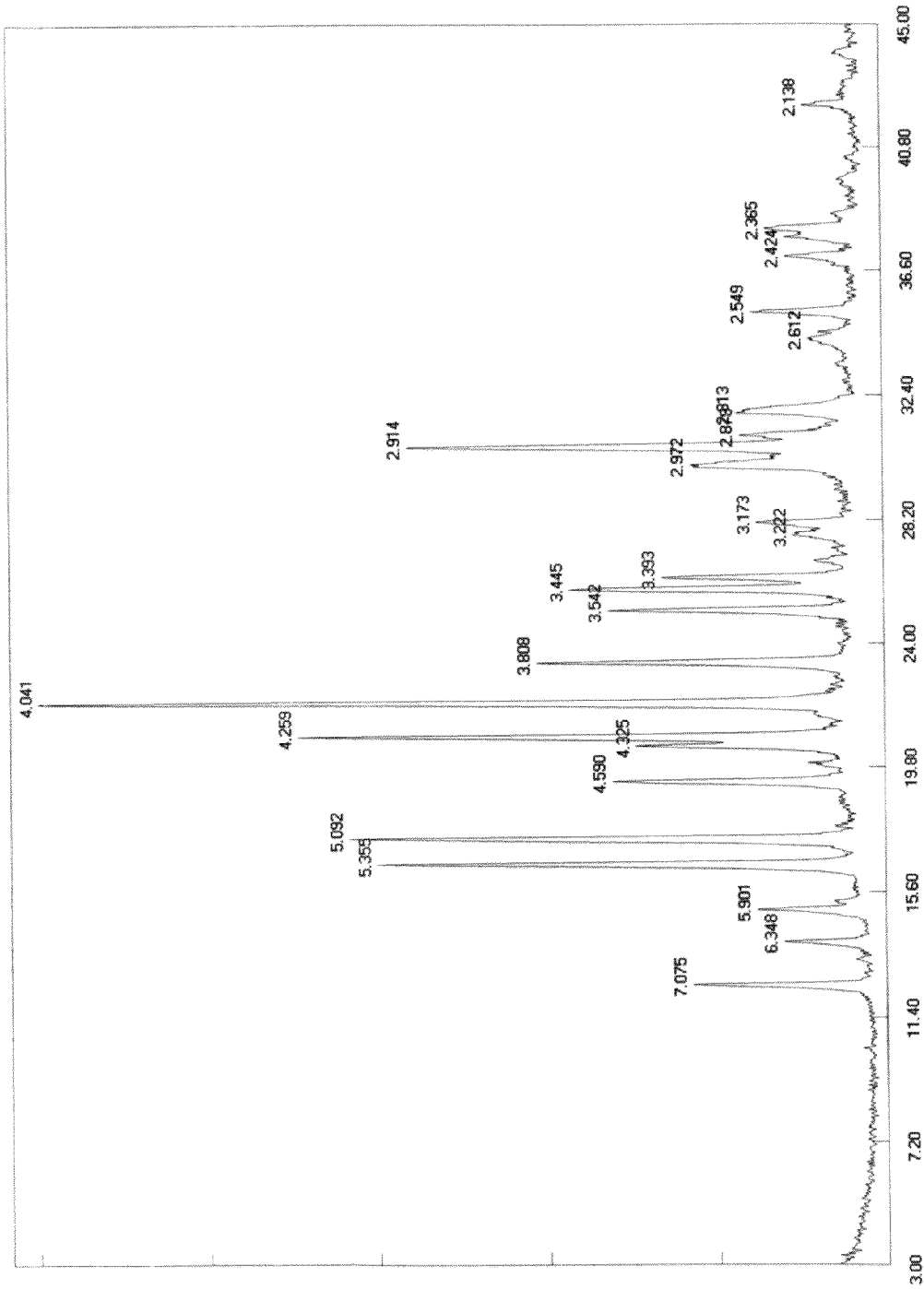
FIG. 1 is a PXRD pattern of a crystal form I of (S)-oxiracetam in accordance with the present invention.
Figure 2:
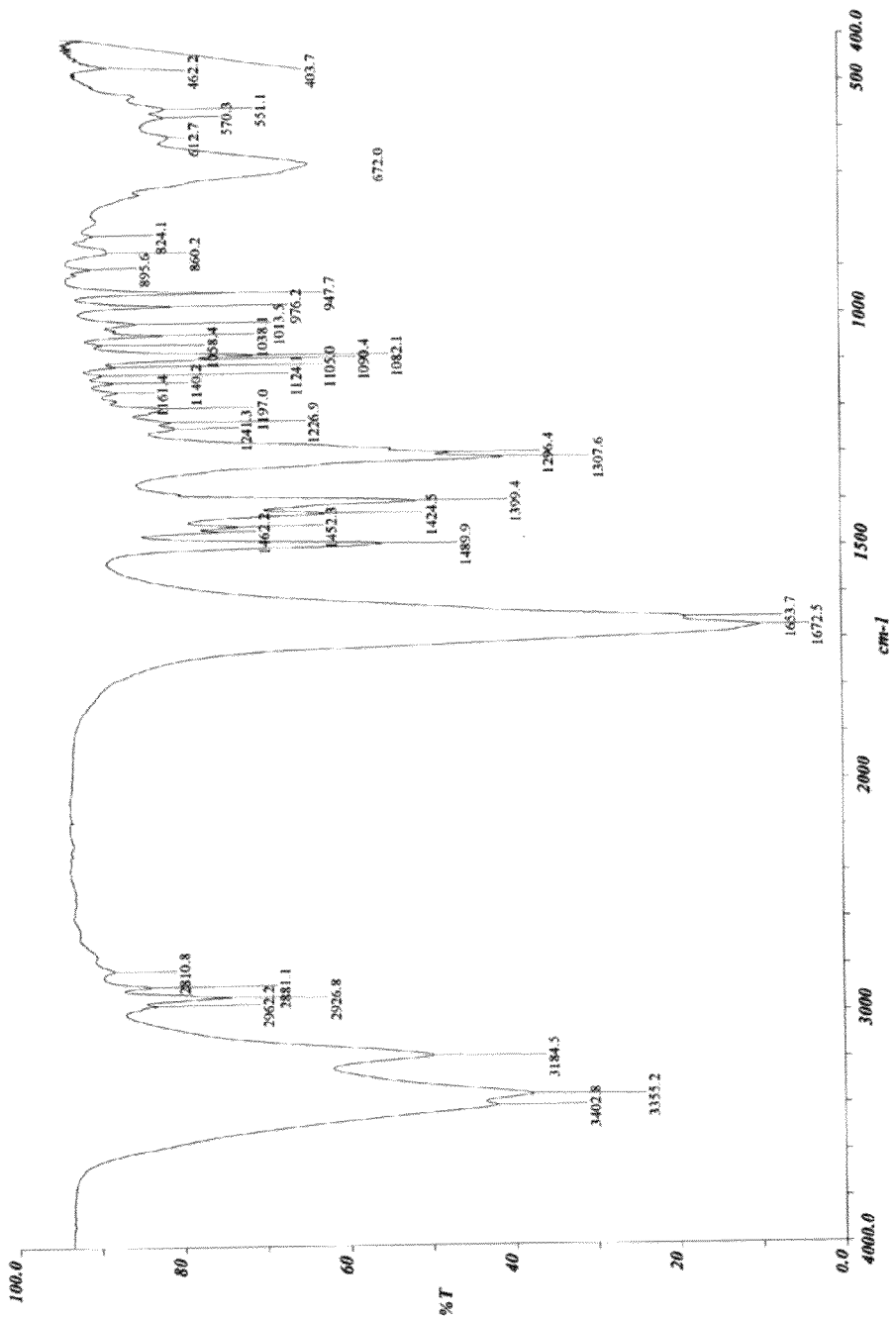
FIG. 2 is an IR spectrum of a crystal form I of (S)-oxiracetam in accordance with the present invention.
Figure 3:
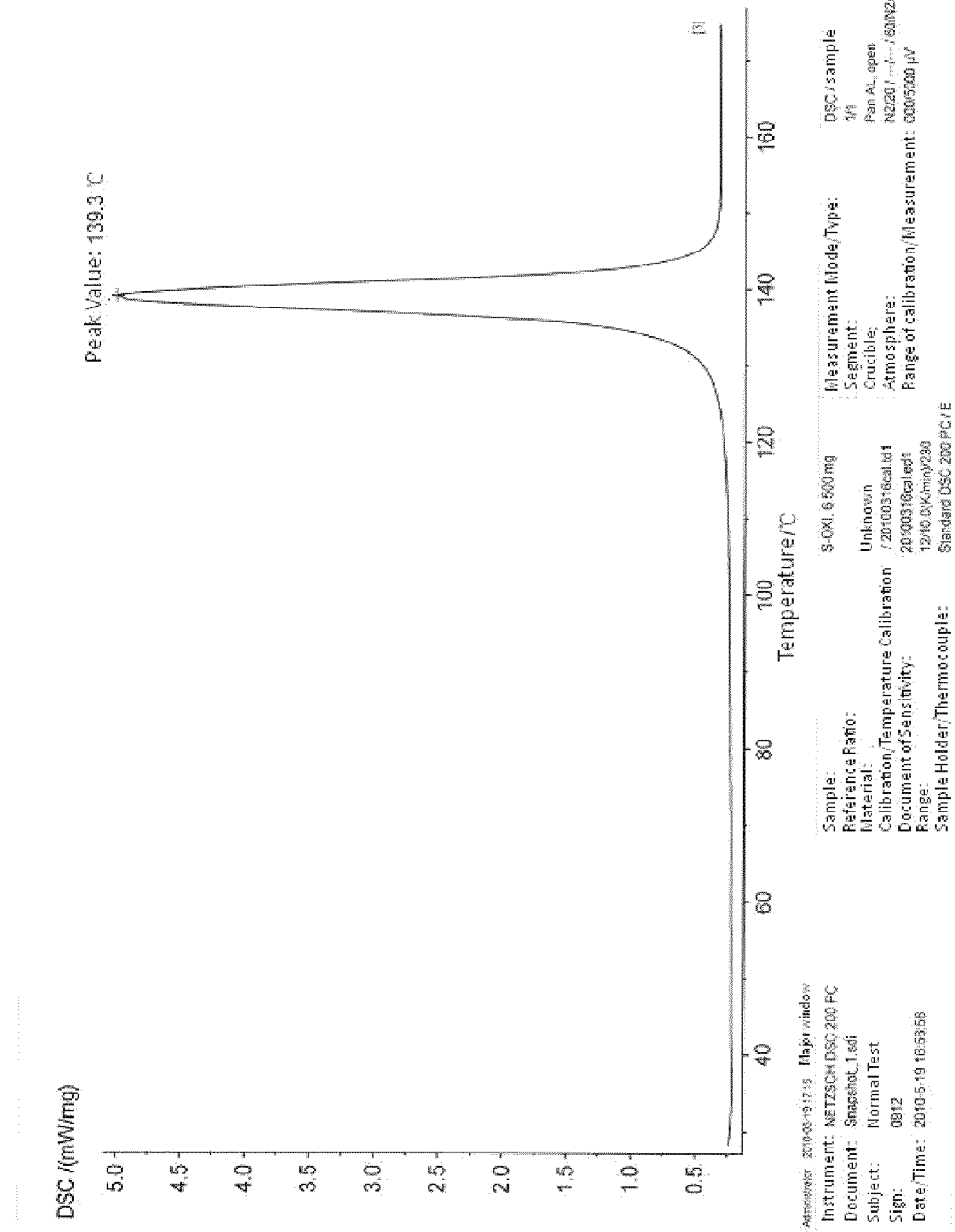
FIG. 3 is a DSC thermogram of a crystal form I of (S)-oxiracetam in accordance with the present invention.

The present invention is more specifically described in the following paragraphs by way of examples. It is necessarily noted that the description, together with details of the structure and function of the invention is illustrative only and not limit the principles of the invention to the embodiments in the disclosure. People skilled in the art will recognize that the invention can be practiced with unessential modification within the spirit and scope of the claims.

Example 1

The method for preparing a crystal form of (S)-oxiracetam in accordance with the present invention comprises steps of:

1. charging 65.0 g glycinamide HCl, 500 ml pure ethanol and 49.3 g sodium bicarbonate into three-necked round-bottom flask, and agitating with increasing the temperature and refluxing;

2. adding 49.3 sodium bicarbonate after refluxing for 2 hours, adding 97.7 g (S)-4-chloro-3-hydroxybutyryl acetate in drops, then refluxing and reacting for 24 hours to form a solution, filtering the solution after it being cooled, and then concentrating the filtered solution to obtain a reddish brown oily substance;

3. dissolving the reddish brown oily substance in 65 ml water and extracting four times with 260 ml methylene dichloride (65 ml methylene dichloride used per time) to obtain a solvent extract, concentrating the solvent extract and removing the remaining methylene dichloride, diluting the concentrated solvent extract and passing it through the 001X7 cation exchange resin, collecting the product fractions of the concentrated solvent extract, neutralizing the product fractions by cation exchange resin 201X7, then filtering the product fractions to remove the remaining resin therein, concentrating the product fractions and adding charcoal in the middle of the process, then agitating for 30 minutes, filtering and concentrating again to obtain a crude product;

4. crystallizing: adding water to the crude product at room temperature, then filtering, agitating with decreasing the temperature to a range of 2° C. to 5° C., adding acetone of a weight 10 times larger than that of water in drops, keeping agitating for 30 minutes at the same temperature, then filtering and washing 2 times with cold acetone to obtain a crystalline product in an amount of 39.6 g;

5. recrystallizing: dissolving the crystalline product in water at room temperature, then filtering and washing the solution 2 or 3 times with cold acetone to make precipitants, keeping adding acetone until the volume of the added acetone is 10 times larger than that of the water, agitating for 30 minutes, then filtering and washing 2 times with cold acetone to obtain a recrystalline product in an amount of 31.6 g and having chromatographic purity: 99.64%, specific rotation: $[\alpha]_D^{20}=-38.0$(C=1.0 for water).

Example 2

1. charging 65.0 g glycinamide HCl, 500 ml pure ethanol and 49.3 g sodium bicarbonate into three-necked round-bottom flask, and agitating with increasing the temperature and refluxing;

2. adding 49.3 sodium bicarbonate after refluxing for 2 hours, adding 97.7 g (S)-4-chloro-3-hydroxybutyryl acetate in drops, then refluxing and reacting for 24 hours to form a solution, filtering the solution after it being cooled, and then concentrating the filtered solution to obtain a reddish brown oily substance;

3. dissolving the reddish brown oily substance in 65 ml water and extracting with 260 ml methylene dichloride to obtain a solvent extract, concentrating the solvent extract and removing the remaining methylene dichloride, diluting the concentrated solvent extract and passing it through the 001X7 cation exchange resin, collecting the product fractions of the concentrated solvent extract, neutralizing the product fractions by cation exchange resin 201X7, then filtering the product fractions to remove the remaining resin therein, concentrating the product fractions and adding charcoal in the middle of the process, then agitating for 30 minutes, filtering and concentrating again to obtain a crude product;

4. refining: adding ethanol of a weight 3 times larger than that of the crude product, then agitating and filtering to obtain a refined crude product;

5. crystallizing: adding water to the refined crude product at room temperature, then filtering, agitating with the decreasing the temperature to a range of 2° C. to 5° C., adding acetone in drops to make precipitants, keeping adding acetone until the volume of the added acetone is 10 times larger than that of the water, agitating for 30 minutes, filtering and then washing 2 times with cold acetone to obtain a crystalline product in an amount of 24.7 g and having chromatographic purity: 99.35%.

Example 3 to 6

The materials and the amounts thereof used in Example 3 to 6 are shown in Table 1, while other factors and steps are all the same as described in Example 1. The produced (S)-oxiracetam has purity of higher than 99.3%, low impurities of about 0-0.5%, based on the percentages of the mass.

Example 7

200 mg crystal form I of (S)-oxiracetam prepared in Example 1, 80.8 mg lactose, 72 mg sodium carboxymethyl starch, 7.2 mg talcum powder and 10% polyvinyl pyrrolidone (PVP) of an appropriate amount for preparing a pharmaceutical composition as a capsule form; for example, a method for preparing 1000 capsules of the pharmaceutical composition with crystal form I of (S)-oxiracetam is described below:

The excipients were sieved with an 80 mesh. Then, the sieved excipients and the crystal form I of (S)-oxiracetam, lactose, sodium carboxymethyl starch in the amount described above were mixed homogeneously to form a mixture. 10% PVP solution was added to the mixture to form a damp mass. The dump mass was processed through pellet fabrication, drying and granulation to form particles. Next, the talcum powder is added into the particles and mixed uniformly, then filled into the capsules.

Example 8

200 mg crystal form I of (S)-oxiracetam prepared in Example 1, 34 mg starch, 60 mg microcrystalline cellulose, 6 mg talcum powder and 2% hydroxypropyl methylcellulose (HPMC) of the K4M type for preparing a pharmaceutical composition as a tablet form; for example, a method for preparing 1000 tablets of the pharmaceutical composition with crystal form I of (S)-oxiracetam is described below:

The excipients were sieved with an 80 mesh. Then, the sieved excipients, the crystal form I of (S)-oxiracetam, starch, the methylcellulose (HPMC) of the K4M type in the amount described above were mixed homogeneously to form a mixture. 2% HPMC solution was added in an appropriate amount to the mixture to form a damp mass. The dump mass was processed through pellet fabrication, drying and granulation to form particles. Next, the talcum powder is added into the particles and mixed uniformly, then compressed to form tablets

Example 9

50 g crystal form I of (S)-oxiracetam prepared in Example 1 and 50 g glucose were diluted in 500 ml water for injection to form a solution, and the temperature of the solution was controlled in a range of between 50° C. and 60° C. The solution was agitated until the solvents were totally dissolved, and the temperature of the solution was decreased to 25° C. The solution was decolorized by adding charcoal, and then the charcoal was removed by filtering. The decolorized solution was added with phosphate buffer to adjusting the pH value being 4.0, and then added with 5000 ml water for injection, encapsulated and sterilized for 30 minutes at 105° C. to obtain an injection.

Example 10

The protective effects of crystal form I of (S)-oxiracetam on memory dysfunction of rats caused by chronic cerebral ischemia.

Material and method: The crystal form I of (S)-oxiracetam prepared in Example 1 and oxiracetam (batch number: 20071101, from Dong Ze Pharmaceutical Science and Technology Co., Ltd., Chong Qing, China) were prepared with normal saline solution freshly on being used.

40 SD male rats were used as experimental animals, and each of them was in a weight of 190 g to 220 g (purchased from Southwest Hospital, Chong Qing, China). The experimental animals were separated into four groups at random (10 animals per group): sham-operation group, cerebral ischemia group, experimental group with treatment of crystal form I of (S)-oxiracetam, control group with treatment of oxiracetam. The experimental group was treated with 100 mg/kg crystal form I of (S)-oxiracetam by intragastric administration, while the control group was treated with 200 mg/kg oxiracetam by intragastric administration, and both of the two group were treated once per day for 37 days since the day of beginning the surgery.

The rats having permanent occlusion of the bilateral carotid arteries were used as model animals of cerebral ischemia group. The cerebral ischemia group, the experimental group and the control group were abdominally anaesthetized by 40 mg/kg pentobarbital natrium. The No. 4 threads were used to separate and ligate the bilateral carotid arteries. The arteries were cut at a position between the near and the far ligation points, and then the wounds made by cut were surgically stitched. The sham-operation group underwent surgery of separation of the bilateral carotid arteries and the wounds made by the surgeries were surgically stitched right away. The body temperature of the animals are maintained during the surgeries.

Morris Water Maze system was used to assayed learning and memory ability of rats (diameter: 120 cm, height: 40 cm; purchased from Institute of Materia Medica (IMM), Chinese Academy of Medical Sciences & Peking Union Medical College). According to the results, the rats of the experimental group had shorter escape latent periods than the model animals of the sham-operation group and the cerebral ischemia group, as well as the rats of the control group treated with racemic oxiracetam. Additionally, the crystal form I of (S)-oxiracetam can greatly increase the swimming time of the rats of the experimental group in the target (35.23±7.03 seconds v.s. 20.18±5.26 seconds, P<0.01). It took 31.23±5.03 seconds for the rats of the control group treated with oxiracetam to swim in the target, a little worse than that of the rats of the experimental group. Therefore, the crystal form of (S)-oxiracetam can significantly improve the cure of the memory dysfunction caused by the cerebral ischemia of the rats, and have better efficacy than racemic oxiracetam.

TABLE 1

| Example | (S)-4-chloro-3-hydroxybutyryl acetate | Glycinamide HCl | The amount of ethanol | The amount of sodium carbonate | Refining and the relative weight of ethanol of the crude product | The materials used in the crystallization (the ratio on the basis of weight parts) | The temperature of the crystallization; time of agitating | Recrystallization |
|---|---|---|---|---|---|---|---|---|
| 3 | 97.7 g | 64.8 g | 500 ml | 98.5 g | Not performed | crude product:water = 1:0.4; water:acetone = 1:20 | −10-5° C.; 2 h | Not performed |

TABLE 1-continued

| Example | (S)-4-chloro-3-hydroxybutyryl acetate | Glycinamide HCl | The amount of ethanol | The amount of sodium carbonate | Refining and the relative weight of ethanol of the crude product | The materials used in the crystallization (the ratio on the basis of weight parts) | The temperature of the crystallization; time of agitating | Recrystallization |
|---|---|---|---|---|---|---|---|---|
| 4 | 78.2 g | 51.8 g | 400 ml | 78.8 g | Not performed | crude product:water = 1:0.7; water:acetone = 1:5 | 8-10° C.; 12 h | Same factors as those of the crystallization in Example 1 |
| 5 | 156.4 g | 103.6 g | 800 ml | 157.6 g | Performed, the amount of ethanol is 8 times larger than the crude product | crude product:water = 1:0.5; water:acetone = 1:10 | 0-5° C.; 5 h | Not performed |
| 6 | 4.9 Kg | 3.3 Kg | 25 L | 4.9 Kg | Performed, the amount of ethanol is 2 times larger than the crude product | crude product:water = 1:0.6; water:acetone = 1:8 | 2-6° C.; 3 h | Not performed |

What is claimed is:

1. A crystal form I of (S)-4-hydroxy-2-oxo-1-pyrrolidine acetamide, characterized by a powder x-ray diffraction pattern that exhibits data of d-values versus the relative intensities (RI) as shown below: TABLE-US-00004 d-value RI d-value RI 7.075 M 5.355 S 5.092 S 4.590 M 4.325 M 4.259 S 4.041 VS 3.808 M 3.542 M 3.445 M 3.393 M 2.972 M 2.914 S wherein VS represents "very strong" intensity; S represents "strong" intensity; M represents "moderately strong" intensity, prepared by steps of preparing crude product and a post-treatment, wherein the post-treatment comprises the step of: crystallizing the crude products using acetone and water as solvents, the water and acetone are in a ratio ranging from 1:5 to 1:20/ based on the weight parts, and the step of crystallizing the crude product is performed at between −10° C. and 10° C., wherein the crystal form is more than 99.3% pure by mass.

2. The crystal form I of (S)-4-hydroxy-2-oxo-1-pyrrolidine acetamide as claimed in claim 1, wherein it is characterized by a powder x-ray diffraction pattern that exhibits data of d-values versus the relative intensities (RI) as shown below: TABLE-US-00005 d-value RI d-value RI 7.075 M 6.348 W 5.901 W 5.355 S 5.092 S 4.590 M 4.325 M 4.259 S 4.041 VS 3.808 M 3.542 M 3.445 M. 3.393 M 3.222 VW 3.171 W. 2.972 M 2.914 S 2.879 W 2.813 W 2.612 VW 2.549 W 2.424 W 2.365 W 2.138 VW wherein VS represents "very strong" intensity; S represents "strong" intensity; M represents "moderately strong" intensity; W represents "weak" intensity; VW represents "very weak" intensity.

3. The crystal form I of (S)-4-hydroxy-2-oxo-1-pyrrolidine acetamide as claimed in claim 1 or 2, wherein it is characterized by a powder x-ray diffraction pattern with peaks at 12.500, 13.940, 15.000, 16.540, 17.400, 19.320, 20.520, 20.840, 21.980, 23.340, 25.120, 25.840, 26.240, 27.660, 28.100, 30.040, 30.660, 31.040, 31.780, 34.300, 35.180, 37.060, 38.020, and 42.240 degrees in terms of 2.theta.

4. The crystal form I of (S)-4-hydroxy-2-oxo-1-pyrrolidine acetamide as claimed in claim 3, wherein it is characterized by characteristic absorption bands obtained from infrared spectroscopy at peaks having the wavelengths (cm.sup.-1) as below: hydroxyl group (.nu..sub.O—H: 3403 cm.sup.-1), amido group (.nu..sub.N—H: 3355 cm.sup.-1, 3184 cm.sup.-1), methylene group (.nu..sub.C—H: 2926 cm.sup.-1, 2881 cm.sup.-1), carbonyl group (.nu..sub.C.dbd.O: 1672 cm.sup.-1, .delta..sub.CH2(scissoring):1489 cm.sup.-1), hydroxyl group (.delta..sub.O—H(in-plane bending): 1399 cm.sup.-1), primary amido group (.delta..sub.N—H: 1307 cm.sup.-1, .delta..sub.C—O: 1082 cm.sup.-1) , primary amido group (.delta..sub.N--H(out-of-plane bending): 672 cm.sup.-1).

5. The crystal form I of (S)-4-hydroxy-2-oxo-1-pyrrolidine acetamide as claimed in claim 1 or 2, wherein it is characterized by characteristic absorption bands obtained from infrared spectroscopy at peaks having the wavelengths (cm.sup.-1) as below: hydroxyl group (.nu..sub.O—H: 3403 cm.sup.-1), amido group (.nu..sub.N—H: 3355 cm.sup.-1, 3184 cm.sup.-1), methylene group (.nu..sub.C--H: 2926 cm.sup.-1, 2881 cm.sup.-1), carbonyl group (.nu..sub.C.dbd.O: 1672 cm.sup.-1, .delta..sub.CH2(scissoring): 1489 cm.sup.-1), hydroxyl group (.delta..sub.O—H(in-plane bending): 1399 cm.sup.-1), primary amido group (.delta..sub.N—H: 1307 cm.sup.-1, .delta..sub.C—O: 1082 cm.sup.-1), primary amido group (.delta..sub.N—H (out-of-plane bending): 672 cm. sup.-1).

6. The crystal form I of (S)-4-hydroxy-2-oxo-1-pyrrolidine acetamide as claimed in claim 4, wherein it has a differential scanning calorimetric peak melting temperature of 139.3.degree. C.

7. A method for preparing the crystal form I of (S)-4-hydroxy-2-oxo-1-pyrrolidine acetamide as claimed in any claim of claims 1 to 6 comprising steps of: preparing crude product and a post-treatment, wherein the post-treatment comprises the step of:
   crystallizing the crude products using acetone and water as solvents
   wherein the water and acetone are in a ratio ranging from 1:5 to 1:20, based on the weight parts, and the step of crystallizing the crude product is performed at between −10° C. and 10° C.

8. The method as claimed in claim 7, wherein the step of crystallizing the crude product is performed at room temperature, and further comprises the steps of: dissolving the crude product in water, filtering, and agitating with decreasing the temperature to a range of between −10.degree. C. and 10.degree.C., then adding acetone in drops, agitating for 0.5 hours to 12 hours at the same temperature, filtering, and washing with cold acetone to obtaining a crystalline product; the crude product and the water are in a ratio ranging from 1:0.4 to 1:0.7.

9. The method as claimed in claim 7 wherein the post-treatment further comprises refining the crude product with ethanol before the step of crystallizing the crude product, which specifically comprises the steps of: adding ethanol in a weight of 2 to 8 times larger than that of the crude product, and agitating and filtering to obtain a refined product; or recrystallizing the crystalline product after the step of crystallizing the crude product.

10. The method as claimed in claim 9, wherein the step of recrystallizing the crystalline product further comprises the steps of: dissolving the crystalline product in water, adding acetone in drops at the temperature of between −10.degree. C. and 10.degree. C., agitating for 0.5 hours to 12 hours to obtain a recrystalline product; the crystalline product and the water are in a ratio of from 1:0.4 to 1:0.7, the water and the acetone are in a ratio of from 1:5 to 1:20, based on the weight parts.

11. The method as claimed in claim 8, further comprising steps of:
  a. mixing glycinamide HC1, pure ethanol and partial or total sodium bicarbonate and agitating with increasing the temperature and refluxing to carry out the reaction;
  b. after refluxing for 2 hours, optionally adding the surplus sodium bicarbonate, and adding (S)-4-chloro-3-hydroxybutyryl acetate in drops, then refluxing and reacting for 24 hours to form a solution, filtering the solution after it being cooled, and then concentrating the filtered solution to make an intermediate product, wherein (S)-4-chloro-3-hydroxybutyryl acetate and glycinamide HCI are in a molar ratio of between 1:0.8 and 1:1.2, (S)-4-chloro-3-hydroxybutyryl acetate and the sodium bicarbonate are in a molar ratio of 1:2, and (S)-4-chloro-3-hydroxybutyryl acetate and the ethanol are in a mole-to-volume ratio of between 1 mole:600 ml and 1 mole:100 ml;
  c. dissolving the intermediate product in water and extracting by using methylene dichloride in a volume of four times larger than that of the water used in dissolving the intermediate product to obtain a solvent extract, concentrating the solvent extract and removing the remaining methylene dichloride, diluting the concentrated solvent extract and passing it through the 001X7 cation exchange resin, collecting product fractions of the concentrated solvent extract, neutralizing the product fractions by cation exchange resin 201X7, then filtering the product fractions to remove the remaining resin therein, concentrating the product fractions and adding charcoal in the middle of the process, then agitating for 30 minutes, filtering and concentrating again to obtain a crude product; and recrystallizing after the crystalizing step by dissolving the crystalline product in water at room temperature, then filtering and washing 2 or 3 times with cold acetone to make precipitants, keeping adding acetone, agitating for 30 minutes, then filtering and washing 2 or 3 times with cold acetone to obtain a recrystalline product; the water and the acetone are in a ratio of ranging from 1:5 to 1:20, based on the weight parts.

12. A pharmaceutical composition for oral treatment, comprising: the crystal form I of (S)-4-hydroxy-2-oxo-1-pyrrolidine acetamide as claimed in any claim of claims 1 to 6; and pharmaceutically acceptable excipients.

13. The pharmaceutical composition for oral treatment as claimed in claim 12, wherein the dosage form thereof is tablets, capsules or injection.

\* \* \* \* \*